United States Patent
Fukushima et al.

(10) Patent No.: US 9,874,545 B2
(45) Date of Patent: Jan. 23, 2018

(54) PHOTOACOUSTIC MICROSCOPE

(71) Applicant: OLYMPUS CORPORATION, Tokyo (JP)

(72) Inventors: Ikutoshi Fukushima, Tokyo (JP); Hisashi Ode, Tokyo (JP); Tomio Endo, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 260 days.

(21) Appl. No.: 14/748,490

(22) Filed: Jun. 24, 2015

(65) Prior Publication Data

US 2015/0316510 A1 Nov. 5, 2015

Related U.S. Application Data

(63) Continuation of application No. PCT/JP2013/005724, filed on Sep. 26, 2013.

(30) Foreign Application Priority Data

| Dec. 25, 2012 | (JP) | 2012-281420 |
| Dec. 25, 2012 | (JP) | 2012-281615 |

(51) Int. Cl.
*G01N 29/26* (2006.01)
*G01N 29/22* (2006.01)
(Continued)

(52) U.S. Cl.
CPC ....... *G01N 29/0681* (2013.01); *G01N 29/221* (2013.01); *G01N 29/2418* (2013.01);
(Continued)

(58) Field of Classification Search
CPC ............. G02B 21/002; G01N 29/0681; G01N 29/221; G01N 29/2418; G01N 29/262;
(Continued)

(56) References Cited

U.S. PATENT DOCUMENTS 4,407,008 A * 9/1983 Schmidt ............. G01N 21/1702
348/79
8,353,830 B2 * 1/2013 Kanayama ........... A61B 5/0091
600/437
(Continued)

FOREIGN PATENT DOCUMENTS

| JP | 01102342 | * | 4/1989 |
| JP | 2005-218684 A | | 8/2005 |
| JP | 2011-519281 A | | 7/2011 |

OTHER PUBLICATIONS

International Search Report dated Dec. 24, 2013 issued in PCT/JP2013/005724.

*Primary Examiner* — J M Saint Surin
(74) *Attorney, Agent, or Firm* — Scully, Scott, Murphy & Presser, P.C.

(57) ABSTRACT

A photoacoustic microscope includes an objective lens that irradiates a specimen with excitation light, a light scanning unit that deflects the excitation light to scan the specimen, an acoustic lens that converts a wavefront of a photoacoustic wave generated by the specimen due to irradiation with the excitation light, a photoacoustic wave detection unit that detects the photoacoustic wave from the acoustic lens, a drive unit that displaces at least one of the acoustic lens and the photoacoustic wave detection unit, and a control unit that controls the drive unit, in synchronization with scanning of the excitation light by the light scanning unit, so that the photoacoustic wave is incident on the photoacoustic wave detection unit perpendicularly.

18 Claims, 18 Drawing Sheets

(51) Int. Cl.
*G01N 29/24* (2006.01)
*G02B 21/00* (2006.01)
*G01N 29/06* (2006.01)

(52) U.S. Cl.
CPC ......... *G01N 29/262* (2013.01); *G02B 21/002* (2013.01); *G01N 2291/02466* (2013.01); *G01N 2291/101* (2013.01); *G01N 2291/106* (2013.01)

(58) Field of Classification Search
CPC ....... G01N 2291/101; G01N 2291/106; G01N 2291/02466
USPC .......................................................... 73/643
See application file for complete search history.

(56) References Cited

U.S. PATENT DOCUMENTS

| | | | |
|---|---|---|---|
| 2005/0187471 A1* | 8/2005 | Kanayama | A61B 5/0091 600/437 |
| 2010/0268042 A1* | 10/2010 | Wang | A61B 5/0059 600/322 |
| 2013/0229493 A1* | 9/2013 | Ikuta | G02B 21/32 348/46 |
| 2015/0085296 A1* | 3/2015 | Ode | G01N 29/0672 356/479 |

* cited by examiner

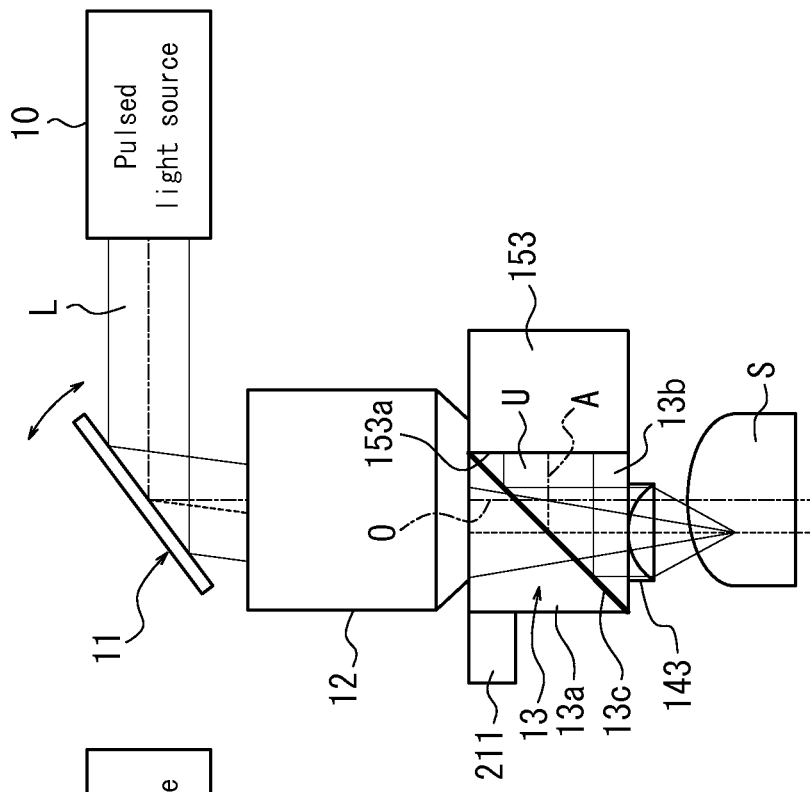
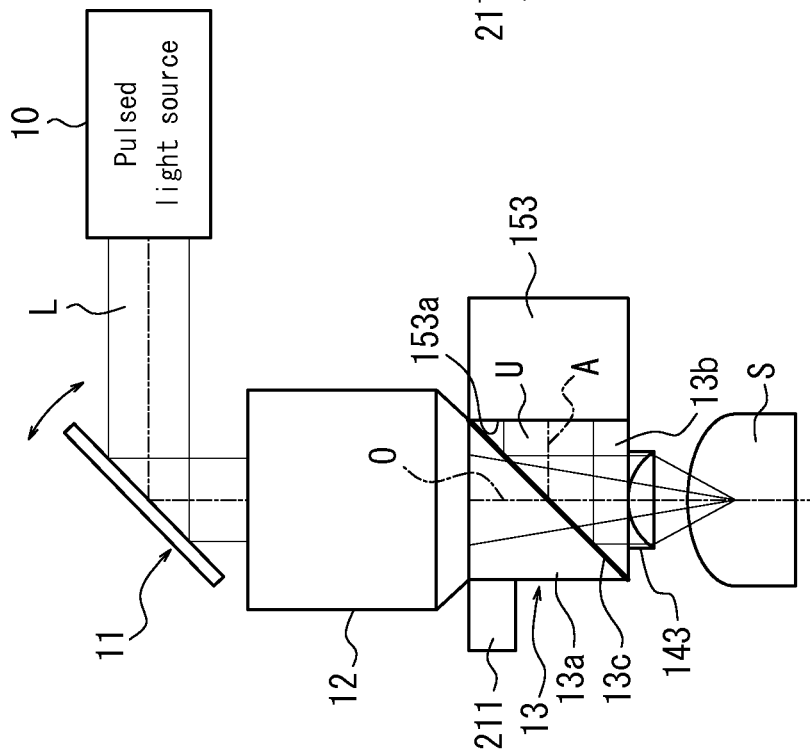

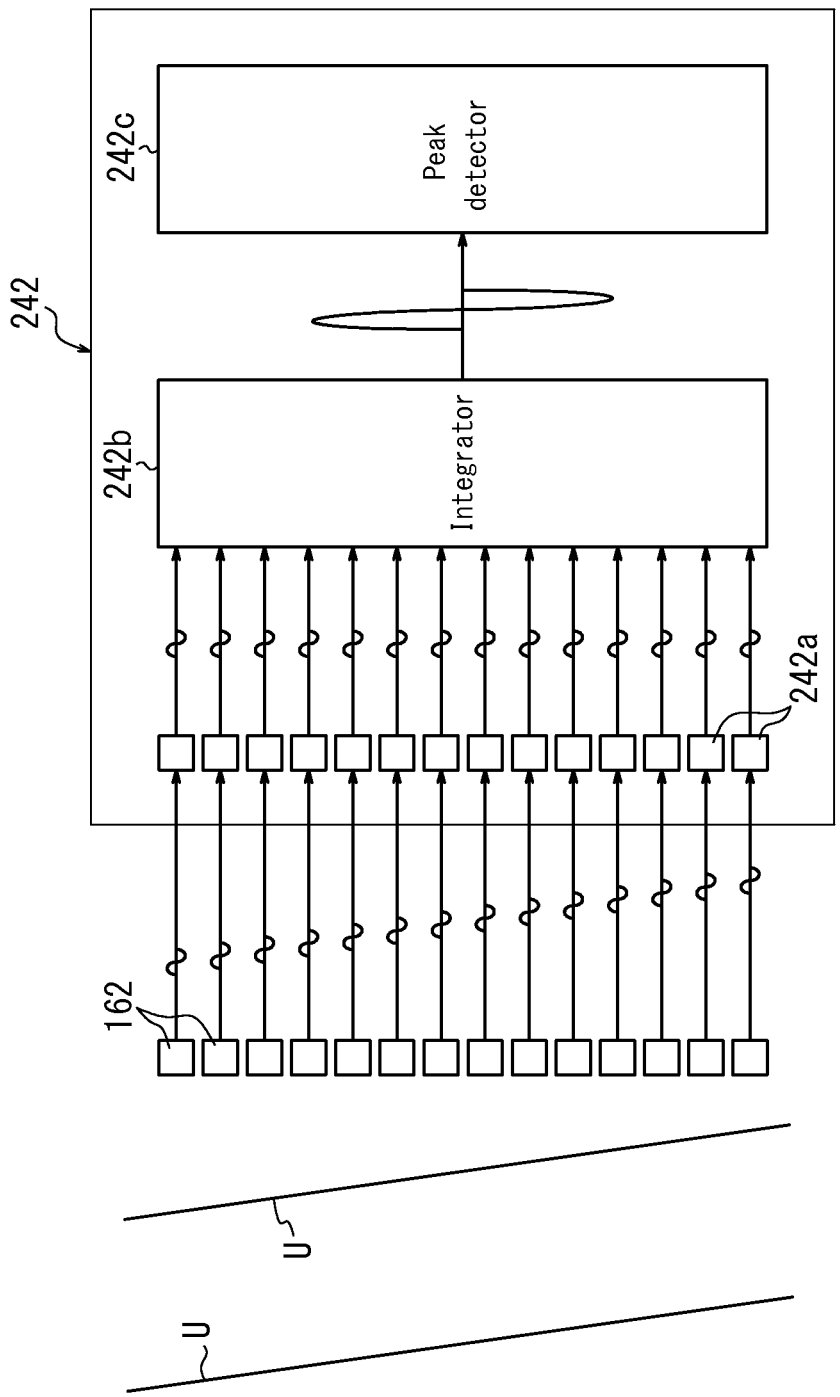

PHOTOACOUSTIC MICROSCOPE

CROSS-REFERENCE TO RELATED APPLICATION

The present application is a Continuing Application based on International Application PCT/JP2013/005724 filed on Sep. 26, 2013, which in turn claims priority to Japanese Patent Applications No. 2012-281615 and No. 2012-281420 filed on Dec. 25, 2012, the entire disclosure of which is incorporated herein by reference.

TECHNICAL FIELD

This disclosure relates to a photoacoustic microscope.

BACKGROUND

Photoacoustic waves are a type of elastic wave occurring during the process of thermoelasticity that takes place when a substance is irradiated with light in an absorption wavelength region. Therefore, photoacoustic waves have attracted attention as a method for imaging absorption properties. Photoacoustic waves are also a type of ultrasonic wave and are less easily affected by diffusion than light is. For these reasons, photoacoustic waves have been applied as a method of imaging the inside of an organism.

In the method used in a photoacoustic microscope for imaging that uses photoacoustic waves as a detection signal, pulsed light adjusted to the absorption wavelength region of the object under observation is used as excitation light, the excitation light is focused by an objective lens, the inside of the specimen is scanned by a focal spot, and the photoacoustic wave occurring at each focal spot as a result is detected with a transducer or the like. With such a photoacoustic microscope, when the specimen is scanned with the focal spot, a photoacoustic wave occurs when an absorbing substance is located at the focal spot position. Hence, by detecting the photoacoustic wave, the absorption properties within the specimen can be imaged.

JP 2011-519281 A (PTL 1), for example, discloses such a photoacoustic microscope. FIG. 18 illustrates the photoacoustic microscope disclosed in PTL 1. In FIG. 18, excitation light L from a non-illustrated laser pulsed light source passes through a focusing lens 101, pinhole 102, vibrating mirror 103, objective lens 104, correcting lens 105, isosceles prism 106, silicone oil layer 107, rhomboid prism 108, and acoustic lens 109 and is focused on the inside of a specimen S. The photoacoustic wave U generated at the focal light position within the specimen S by irradiation of the excitation light L undergoes wavefront conversion by the acoustic lens 109, is reflected within the rhomboid prism 108, and is detected by an ultrasonic transducer 110.

In FIG. 18, the isosceles prism 106 and the rhomboid prism 108 are joined with the silicone oil layer 107 therebetween. The acoustic lens 109 is joined to the rhomboid prism 108 so that the acoustic axis, which corresponds to the optical axis in an optical lens, matches the optical axis of the objective lens 104, and so that the acoustic wave focusing position of the acoustic lens 109 and the focal light position of the excitation light L within the specimen S match. The ultrasonic transducer 110 is joined to the rhomboid prism 108 so that the wavefront of the photoacoustic wave U from the focal point of the acoustic lens 109 is converted to a plane wave by the acoustic lens 109 and is perpendicularly incident on the detection surface of the ultrasonic transducer 110. The specimen S is immersed in liquid.

CITATION LIST

Patent Literature

PTL 1: JP 2011-519281 A

In a photoacoustic microscope structured as in FIG. 18, the excitation light L shone on the specimen S is deflected by vibrating the vibrating mirror 103, and the specimen S is scanned by the focal spot of the excitation light L. Upon deflecting the excitation light L with the vibrating mirror 103, however, the excitation light L forms a focal spot at a position that deviates from the acoustic wave focusing position of the acoustic lens 109. After undergoing wavefront conversion in the acoustic lens 109, the photoacoustic wave U generated at a location that deviates from the acoustic wave focusing position of the acoustic lens 109 is incident on the detection surface of the ultrasonic transducer 110 at an inclination with respect to the detection surface.

The ultrasonic transducer 110 is set so that the detection sensitivity is highest when a plane wave is incident perpendicularly. Therefore, upon attempting to expand the scan range of the specimen S with the reflecting mirror 103, the maximum inclination of the photoacoustic wave U incident on the ultrasonic transducer 110 increases and the detection accuracy lowers. Instead of scanning by using the reflecting mirror 103, an excitation light L incidence system including the objective lens 104 and a photoacoustic wave U detection system including the acoustic lens 109 could be moved relative to a specimen stage on which the specimen S is mounted, so that the photoacoustic wave U from the specimen S is always incident on the ultrasonic transducer 110 perpendicularly. Doing so, however, would prolong the scanning.

It could therefore be helpful to provide a photoacoustic microscope that allows for high-speed scanning and that can improve detection accuracy over a wide scanning range.

SUMMARY

A photoacoustic microscope according to a first aspect of this disclosure includes:

an objective lens configured to irradiate a specimen with excitation light;

a light scanning unit configured to deflect the excitation light to scan the specimen;

an acoustic lens configured to convert a wavefront of a photoacoustic wave generated by the specimen due to irradiation with the excitation light;

a photoacoustic wave detection unit configured to detect the photoacoustic wave from the acoustic lens;

a drive unit configured to displace at least one of the acoustic lens and the photoacoustic wave detection unit; and a control unit configured to control the drive unit, in synchronization with scanning of the excitation light by the light scanning unit, so that the photoacoustic wave is incident on the photoacoustic wave detection unit perpendicularly.

A photoacoustic microscope according to a second aspect of this disclosure includes:

an objective lens configured to irradiate a specimen with excitation light;

a light scanning unit configured to deflect the excitation light to scan the specimen along at least a first scanning direction;

a photoacoustic wave detection unit comprising a plurality of detectors that detect a photoacoustic wave generated by the specimen due to irradiation with the excitation light, the detectors being arranged along a first array direction corresponding to the first scanning direction;

a combination unit configured to combine a phase of the photoacoustic wave detected by each detector;

an acoustic lens configured to convert a wavefront of the photoacoustic wave generated by the specimen due to irradiation with the excitation light;

a drive unit configured to displace at least one of the acoustic lens and the photoacoustic wave detection unit; and a control unit configured to control the drive unit, in synchronization with scanning of the excitation light along a second scanning direction by the light scanning unit, so that the photoacoustic wave is incident on the photoacoustic wave detection unit perpendicularly, wherein the light scanning unit also deflects the excitation light in the second scanning direction which differs from the first scanning direction, and wherein the detectors detect the photoacoustic wave that has the wavefront converted by the acoustic lens.

We thus provide a photoacoustic microscope that allows for high-speed scanning and that can improve detection accuracy over a wide scanning range.

BRIEF DESCRIPTION OF THE DRAWINGS

In the accompanying drawings:

FIGS. 13A and 13B illustrate operation of the drive unit in FIG. 11;

FIG. 14 illustrates phase adjustment in the combination unit when the photoacoustic wave is detected as a plane wave;

DETAILED DESCRIPTION

The following describes embodiments with reference to the drawings.

Embodiment 1

Figure 1:
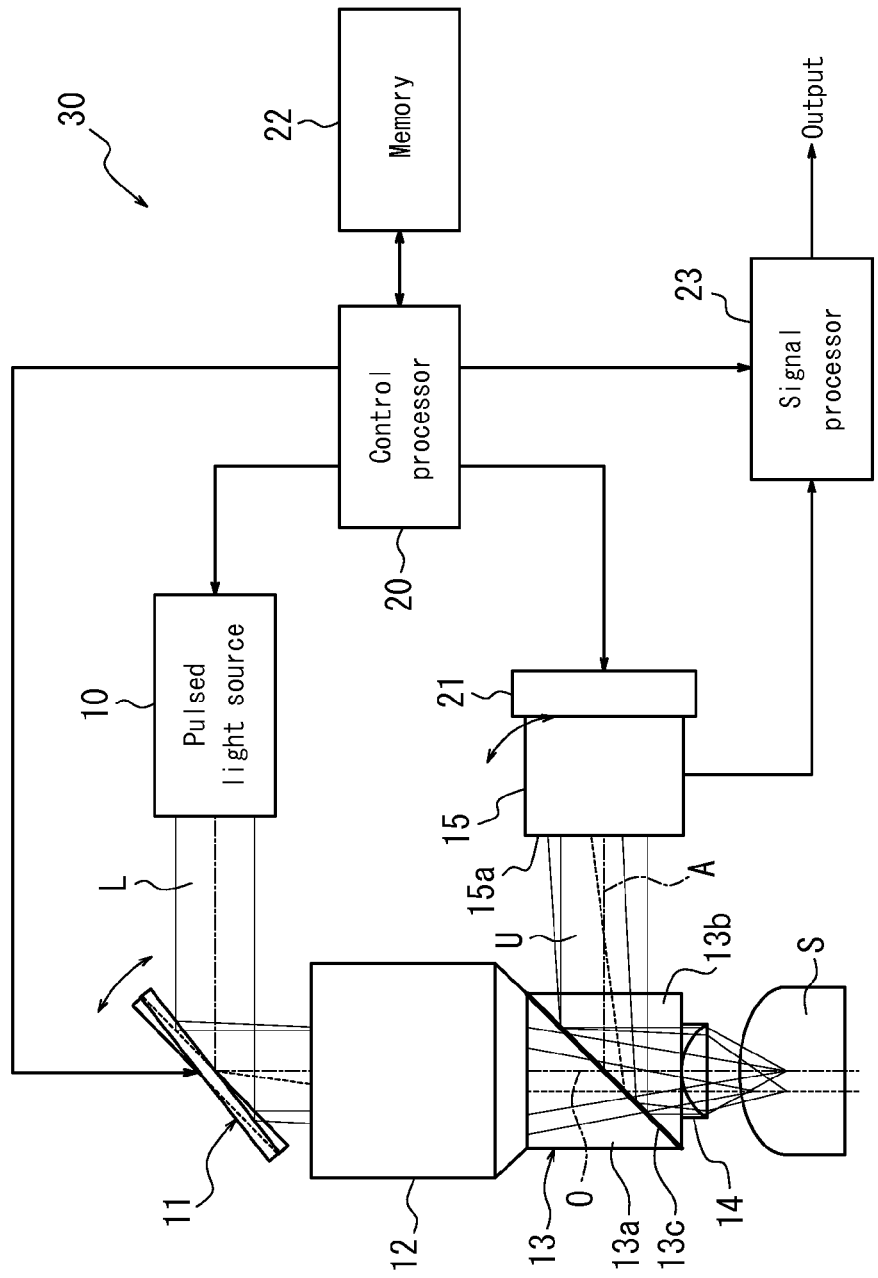
FIG. 1 schematically illustrates the structure of a section of a photoacoustic microscope according to Embodiment 1.

FIG. 1 schematically illustrates the structure of a section of a photoacoustic microscope according to Embodiment 1. A photoacoustic microscope 30 according to this embodiment uses a light scanning unit 11 to deflect excitation light L emitted from a pulsed light source 10, and using an objective lens 12, passes the excitation light L through a photoacoustic wave reflector 13 and an acoustic lens 14 to irradiate the inside of a specimen S as a focal spot. A photoacoustic wave U generated in the specimen S undergoes wavefront conversion to a plane wave by the acoustic lens 14 and is then reflected by the photoacoustic wave reflector 13 in a different direction than the optical path of the excitation light L and is detected by a photoacoustic wave detection unit 15.

When, for example, the specimen S is a living organism, and a blood vessel within the living organism is being imaged, then the pulsed light source 10 emits excitation light L at the absorption wavelength of hemoglobin. The target of observation is not limited to a blood vessel. The photoacoustic microscope 30 may be adopted for imaging an endogenous substance such as melanin. In this case, it suffices to use light in the absorption wavelength region of the targeted substance as the excitation light L. The photoacoustic microscope 30 may also be adopted for imaging of an exogenous substance such as a fluorescent substance or metallic nanoparticles. In this case, it suffices to use light in the absorption wavelength region of the targeted fluorescent substance or light in the resonant wavelength region of the targeted metallic nanoparticles as the excitation light L. When a plurality of absorbers are located within the specimen S, it is preferable to use light at the peak wavelength of the characteristic absorption spectrum of the object under observation. In the pulsed light source 10, the emission timing of the pulsed light is controlled by a control processor 20.

The light scanning unit 11 for example includes two galvanometer mirrors, the driving of which is controlled by the control processor 20 in synchronization with the emission timing of the pulsed light source 10, so that the inside of the specimen S is two-dimensionally scanned by the focal spot of the excitation light L.

As the objective lens 12, lenses with different focal lengths are appropriately selected and mounted.

The photoacoustic wave reflector 13 includes two right triangular prisms 13a and 13b, the inclined faces of which are joined by a photoacoustic wave reflection member 13c. The photoacoustic wave reflection member 13c is transparent with respect to the excitation light L and is formed from a member with a different acoustic impedance than the right triangular prism 13b at the acoustic lens 14 side, such as silicone oil or air. Since the difference between the acoustic impedance of the right triangular prism 13b and the acoustic impedance of the photoacoustic wave reflection member 13c satisfies a predetermined relationship, the photoacoustic wave U is reflected by the photoacoustic wave reflection member 13c.

The acoustic lens 14 is joined to the exit face of the excitation light L in the right triangular prism 13b so that an acoustic axis A, which corresponds to the optical axis of an optical lens, is coaxial with an optical axis O of the objective lens 12. The acoustic wave focusing position of the acoustic lens 14 approximately matches the focusing position of the optical system constituted by the objective lens 12, photoacoustic wave reflector 13, and acoustic lens 14. In this way, the photoacoustic wave U generated at the focal spot position of the excitation light L in the specimen S is converted to a plane wave by the acoustic lens 14 and is incident on the right triangular prism 13b. At the interface between the right triangular prism 13b and the photoacoustic wave reflection member 13c, the photoacoustic wave U is reflected in a different direction than the optical path of the excitation light L, exits from the right triangular prism 13b, and is detected by the photoacoustic wave detection unit 15. The space between at least the objective lens 12 and the specimen S and between the right triangular prism 13b and the photoacoustic wave detection unit 15 is preferably filled with a photoacoustic wave transmission medium, such as water, glycerin, or the like, through which the photoacoustic wave U easily propagates.

The photoacoustic wave detection unit 15 is, for example, an ultrasonic transducer. In this embodiment, the photoacoustic wave detection unit 15 is configured to be displaceable by a drive unit 21. The drive unit 21 is, for example, provided with a gimbal actuator that, in synchronization with scanning of the excitation light L by the light scanning unit 11, controls the inclination of a detection surface 15a of the photoacoustic wave detection unit 15 with respect to the acoustic axis A of the acoustic lens 14 based on a control amount from the control processor 20, so that the photoacoustic wave U is incident on the photoacoustic wave detection unit 15 perpendicularly.

The control processor 20 controls overall operations by the photoacoustic microscope 30. A memory 22 is connected to the control processor 20. The memory 22 stores a database compilation of the control amount of the drive unit 21 that is synchronized with scanning of the excitation light L by the light scanning unit 11 in association with the focal length of objective lenses that can be mounted in the photoacoustic microscope 30. The control amount represents the displacement amount of the detection surface 15a of the photoacoustic wave detection unit 15. This displacement amount includes the direction in which the detection surface 15a is inclined and the amount of inclination. The control processor 20 reads the control amount (displacement amount) corresponding to the focal length of the mounted objective lens 12 from the memory 22 and controls the drive unit 21 in synchronization with scanning of the excitation light L by the light scanning unit 11. An operation program and the like for the control processor 20 are stored in the memory 22 as necessary. The memory 22 may be internal memory of the control processor 20.

A signal processor 23 is also connected to the control processor 20. In synchronization with the driving of the light scanning unit 11 by the control processor 20, i.e. in synchronization with the irradiation timing of the excitation light L when two-dimensionally scanning the specimen S in a plane orthogonal to the optical axis O of the objective lens 12, the signal processor 23 converts, based on an output signal obtained from the photoacoustic wave detection unit 15, the correspondence relationship between the irradiation position of the excitation light L and the output signal into data. For example, the irradiation position of the excitation light L and the acquired signal strength may be associated, or the irradiation position of the excitation light L and the acquired output waveform may be associated. When converting data on the scanned surface of the specimen S into an image, the signal processor 23 generates the image, and the image may, for example, be stored in an image memory and displayed on a monitor, although this configuration is not illustrated in the drawings. The signal processor 23 may be internal to the control processor 20.

Figure 2A:
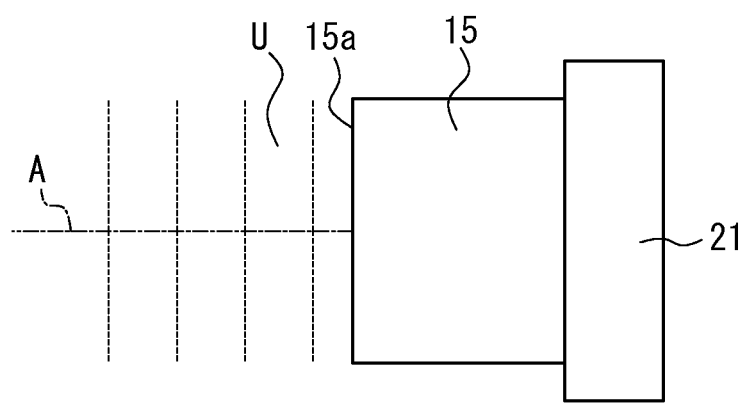
FIGS. 2A and 2B are partially enlarged views illustrating operation of the photoacoustic microscope in FIG. 1.
Figure 2B:
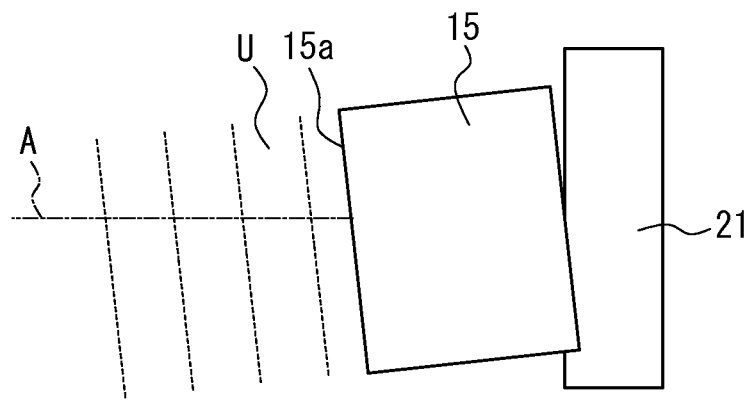

In the photoacoustic microscope according to this embodiment, in synchronization with scanning of the excitation light L by the light scanning unit 11, inclination of the detection surface 15a is controlled so that a plane wave of the photoacoustic wave U from the specimen S is incident on the detection surface 15a of the photoacoustic wave detection unit 15 perpendicularly. In other words, at a drive position of the light scanning unit 11 such that the focal spot of the excitation light L is formed at nearly the focusing position of the acoustic lens 14, the detection surface 15a of the photoacoustic wave detection unit 15 is controlled to be orthogonal to the acoustic axis A of the acoustic lens 14, as illustrated by the partially enlarged view in FIG. 2A. At a drive position of the light scanning unit 11 such that the focal spot of the excitation light L is separated from the focusing position of the acoustic lens 14, the detection surface 15a of the photoacoustic wave detection unit 15 is controlled to be inclined with respect to the acoustic axis A of the acoustic lens 14, as illustrated by the partially enlarged view in FIG. 2B. The displacement amount of the detection surface 15a with respect to the acoustic axis A, i.e. the amount and direction of inclination of the detection surface 15a, is changed in accordance with the distance and direction of separation of the focal spot from the acoustic wave focusing position of the acoustic lens 14.

Therefore, according to the photoacoustic microscope of this embodiment, the detection accuracy of the photoacoustic wave U from the specimen S can be improved across a wide scanning range of the specimen S. Scanning the specimen S by deflecting excitation light L with the light scanning unit 11 allows for high-speed scanning. Furthermore, since the control amount of the drive unit 21 with respect to the focal length of mountable objective lenses is stored in the memory 22, the use of objective lenses with a variety of focal lengths can easily be accommodated.

Embodiment 2

Figure 3:
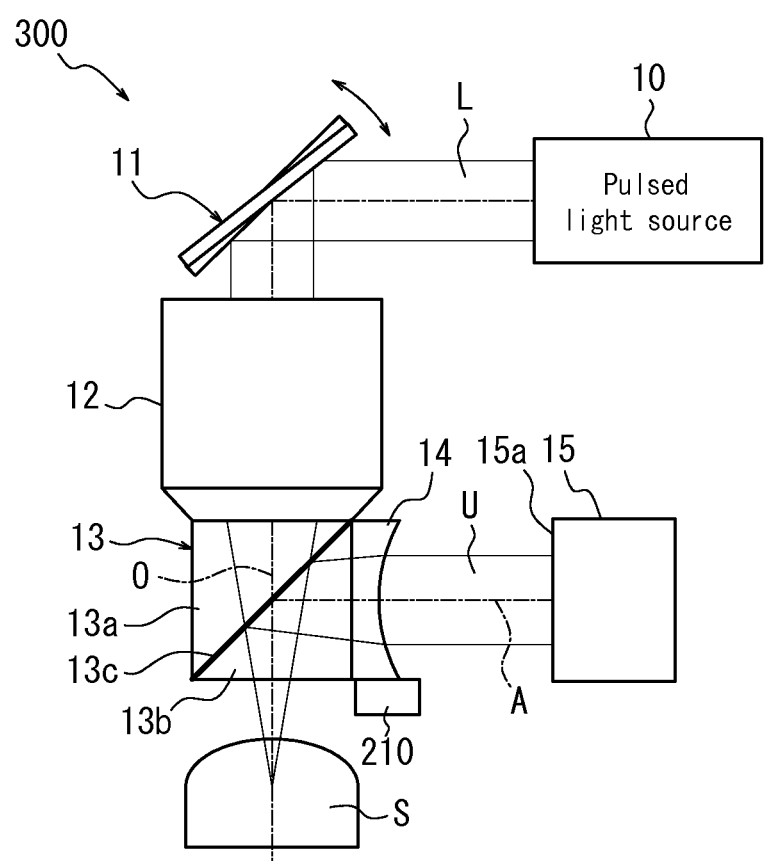
FIG. 3 schematically illustrates the structure of a section of a photoacoustic microscope according to Embodiment 2.

FIG. 3 schematically illustrates the structure of a section of a photoacoustic microscope according to Embodiment 2. A photoacoustic microscope 300 according to this embodiment has a structure resembling that of the photoacoustic microscope illustrated in FIG. 1, yet the photoacoustic wave detection unit 15 is fixed in place. The acoustic lens 14 is also joined displaceably to the exit face of the photoacoustic wave U in the right triangular prism 13b, and along the exit face, i.e. in a plane orthogonal to the acoustic axis A, the acoustic lens 14 is moved by a drive unit 210. The drive unit 210 for example includes two piezo actuators or two stepping motors that, based on the control amount from the control processor 20 (see FIG. 1), move the acoustic lens 14 two-dimensionally in correspondence with two-dimensional scanning of the specimen S by the excitation light L. The photoacoustic wave detection unit 15 is disposed so that the detection surface 15a is orthogonal to the acoustic axis of the acoustic lens 14. Since the remaining structure is similar to that of Embodiment 1, structural elements operating in the same way as the structural elements illustrated in FIG. 1 are labeled with the same reference signs, and a description thereof is omitted. The control processor 20, memory 22, and signal processor 23 illustrated in FIG. 1 are omitted from FIG. 3 for the sake of clarity.

Figure 4A:
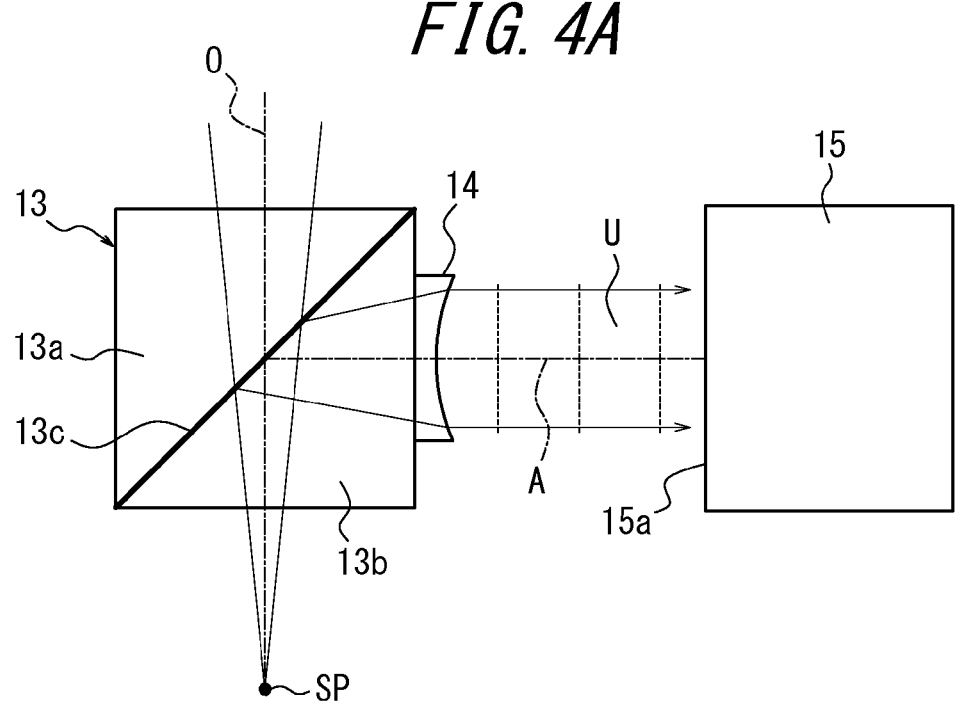
FIGS. 4A and 4B are partially enlarged views illustrating operation of the photoacoustic microscope in FIG. 3.
Figure 4B:
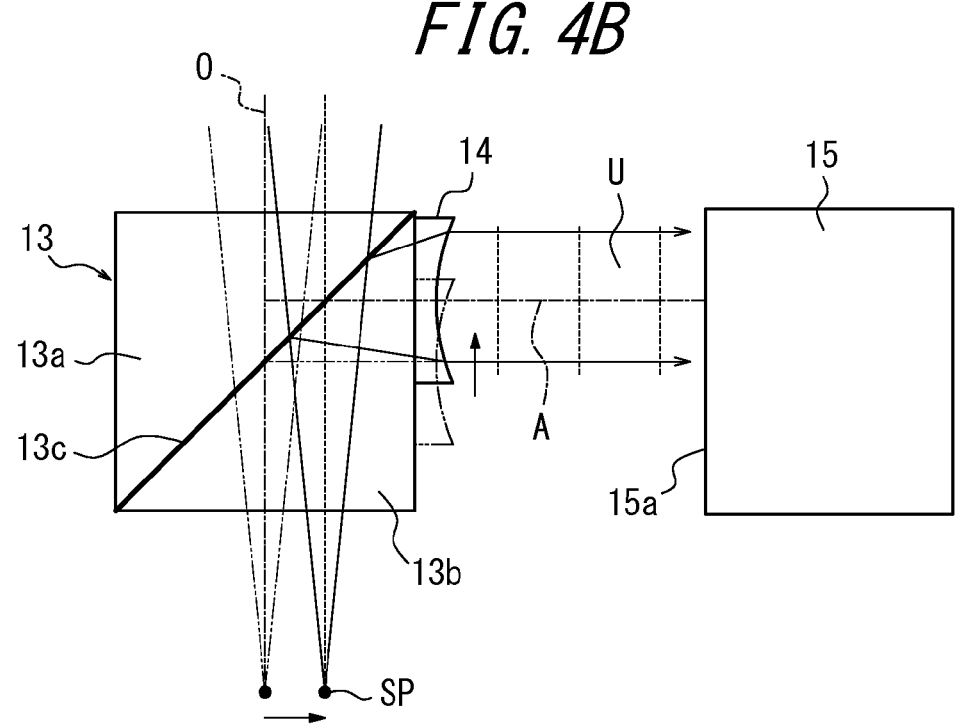

In the photoacoustic microscope according to this embodiment, in synchronization with scanning of the excitation light L by the light scanning unit 11, the acoustic lens 14 is moved by the drive unit 210 in a plane orthogonal to the acoustic axis A, so that a plane wave of the photoacoustic wave U from the specimen S is incident on the detection surface 15a of the photoacoustic wave detection unit 15 perpendicularly. In other words, at a drive position of the light scanning unit 11 such that the focal spot of the excitation light L is formed along the optical axis O of the objective lens 12, the acoustic lens 14 is controlled so that the focusing position of the acoustic lens 14 matches the focal spot position SP of the excitation light L, as illustrated in the partially enlarged view in FIG. 4A. At a drive position of the light scanning unit 11 such that the focal spot of the excitation light L is formed at a distance from the optical axis O of the objective lens 12, the acoustic lens 14 is controlled so that the focusing position of the acoustic lens 14 matches the focal spot position SP of the excitation light L that is at a distance from the optical axis O, as illustrated in the partially enlarged view in FIG. 4B. Therefore, in this embodiment, in synchronization with scanning of the excitation light L by the light scanning unit 11, the acoustic lens 14 is moved by the drive unit 210 two-dimensionally in a plane orthogonal to the acoustic axis A, so that the focusing position of the acoustic lens 14 matches the focal spot position SP of the excitation light L.

Hence, the photoacoustic microscope according to this embodiment achieves effects similar to those of the photoacoustic microscope according to Embodiment 1.

Embodiment 3

Figure 5A:
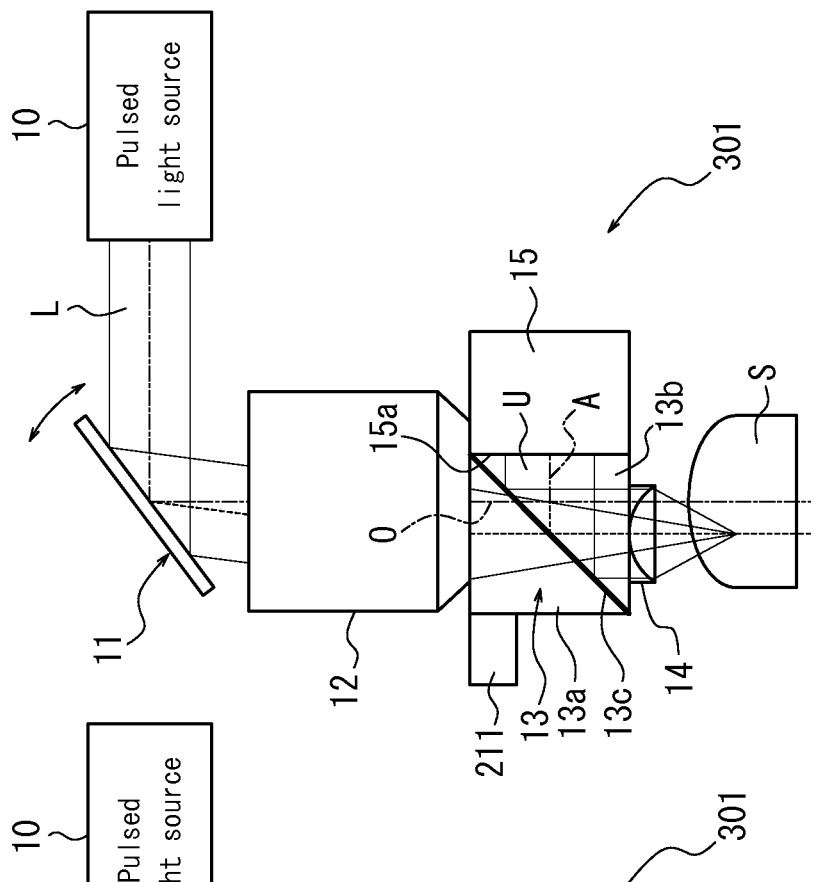
FIGS. 5A and 5B schematically illustrate the structure of a section of a photoacoustic microscope according to Embodiment 3.
Figure 5B:
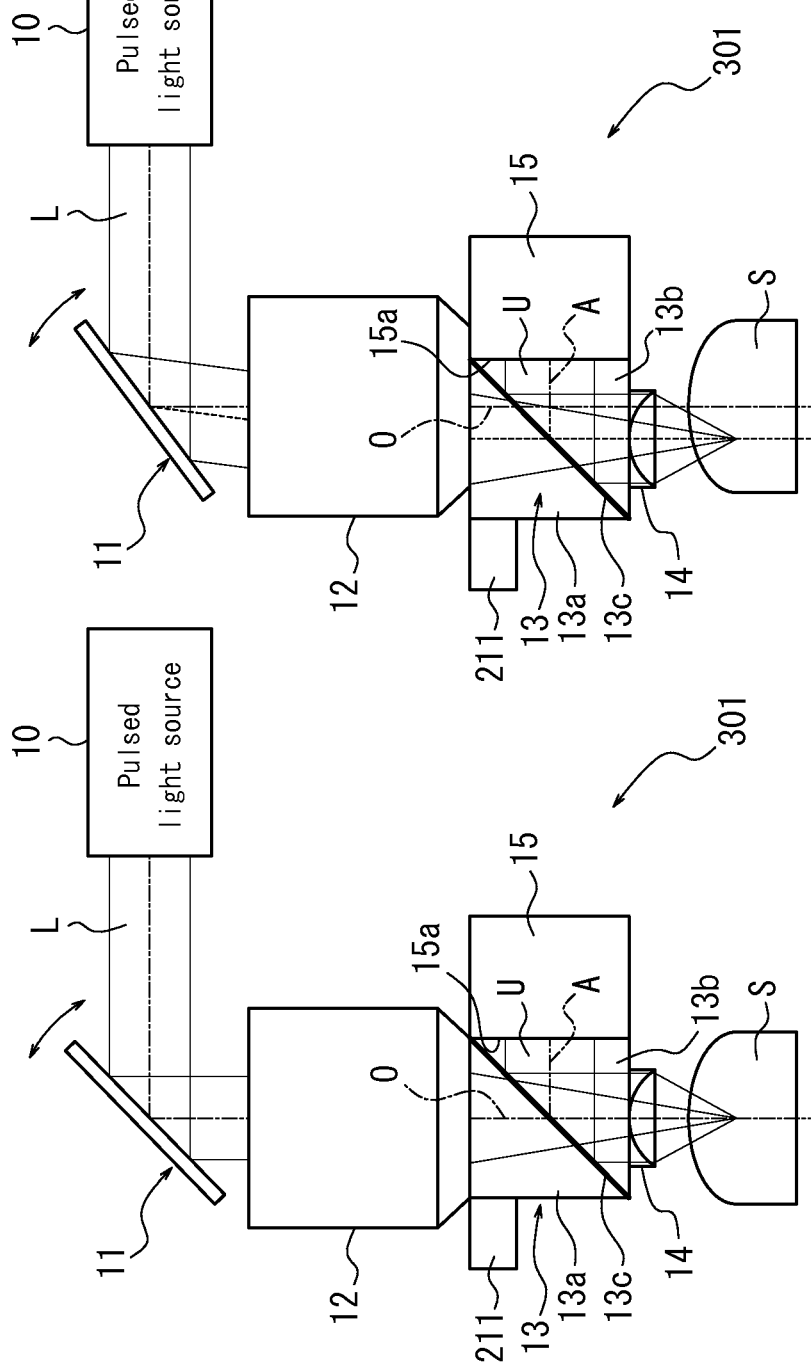

FIGS. 5A and 5B schematically illustrate the structure of a section of a photoacoustic microscope according to Embodiment 3. A photoacoustic microscope 301 according to this embodiment has a structure resembling that of the photoacoustic microscope illustrated in FIG. 1, yet the photoacoustic wave detection unit 15 is joined to the exit face of the photoacoustic wave U in the right triangular prism 13b, so that the acoustic axis A of the acoustic lens 14 and the detection surface 15a are orthogonal. Also, the acoustic lens 14 is moved by the drive unit 211 integrally with the photoacoustic wave reflector 13 and the photoacoustic wave detection unit 15 in a plane orthogonal to the acoustic axis A. As in Embodiment 2, the drive unit 211 for example includes two piezo actuators or two stepping motors that, based on the control amount from the control processor 20 (see FIG. 1), move the photoacoustic wave reflector 13, acoustic lens 14, and photoacoustic wave detection unit 15 integrally in the direction of two-dimensional scanning of the specimen S by the excitation light L. Since the remaining structure is similar to that of Embodiment 1, structural elements operating in the same way as the structural elements illustrated in FIG. 1 are labeled with the same reference signs, and a description thereof is omitted. The control processor 20, memory 22, and signal processor 23 illustrated in FIG. 1 are omitted from FIGS. 5A and 5B for the sake of clarity.

In the photoacoustic microscope according to this embodiment, in synchronization with scanning of the excitation light L by the light scanning unit 11, the photoacoustic wave reflector 13, acoustic lens 14, and photoacoustic wave detection unit 15 are moved integrally by the drive unit 211 in a plane orthogonal to the acoustic axis A, so that a plane wave of the photoacoustic wave U from the specimen S is incident on the detection surface 15a of the photoacoustic wave detection unit 15 perpendicularly. In other words, at a drive position of the light scanning unit 11 such that the focal spot of the excitation light L is formed along the optical axis O of the objective lens 12, the acoustic wave focusing position of the acoustic lens 14 is controlled to match the focal spot position of the excitation light L, as illustrated in FIG. 5A. At a drive position of the light scanning unit 11 such that the focal spot of the excitation light L is formed at a distance from the optical axis O of the objective lens 12, the acoustic wave focusing position of the acoustic lens 14 is controlled to match the focal spot position of the excitation light L that is at a distance from the optical axis O, as illustrated in FIG. 5B. Therefore, in this embodiment, in synchronization with scanning of the excitation light L by the light scanning unit 11, the acoustic lens 14 is moved by the drive unit 211 integrally with the photoacoustic wave reflector 13 and photoacoustic wave detection unit 15 two-dimensionally in a plane orthogonal to the acoustic axis A, so that the focusing position of the acoustic lens 14 matches the focal spot position of the excitation light L.

Hence, the photoacoustic microscope according to this embodiment achieves effects similar to those of the photoacoustic microscope according to Embodiment 1.

Embodiment 4

Next, Embodiment 4 is described. Embodiment 4 differs from Embodiment 1 by not including an acoustic lens. The structure of the photoacoustic wave detection unit and the function of the control processor also differ. The following description of Embodiment 4 focuses on the differences from Embodiment 1. Components that have the same structure as in Embodiment 1 are labeled with the same reference signs.

Figure 6:
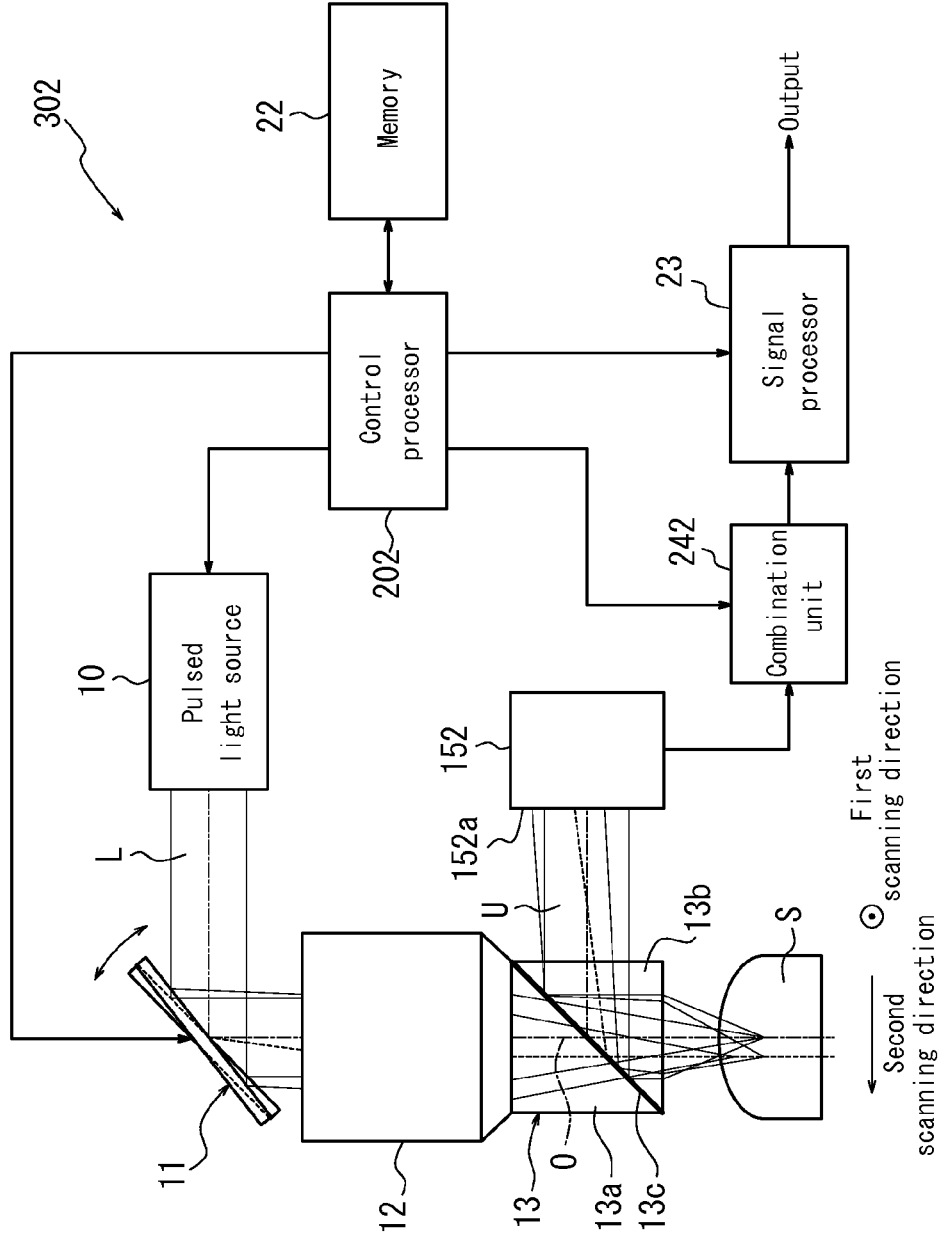
FIG. 6 schematically illustrates the structure of a section of a photoacoustic microscope according to Embodiment 4.

FIG. 6 schematically illustrates the structure of a section of a photoacoustic microscope according to Embodiment 4. A photoacoustic microscope 302 uses a light scanning unit 11 to deflect excitation light L emitted from a pulsed light source 10, and using an objective lens 12, passes the excitation light L through a photoacoustic wave reflector 13 to irradiate the inside of a specimen S as a focal spot. A photoacoustic wave U generated in the specimen S is reflected by the photoacoustic wave reflector 13 in a different direction than the optical path of the excitation light L and is detected by a photoacoustic wave detection unit 152.

The light scanning unit 11 for example includes two galvanometer mirrors, the driving of which is controlled by a control processor 202 in synchronization with the emission timing of the pulsed light source 10, so that the inside of the specimen S is two-dimensionally scanned by the focal spot of the excitation light L along a first scanning direction and a second scanning direction.

The photoacoustic wave reflector 13 includes two right triangular prisms 13a and 13b, the inclined faces of which are joined by a photoacoustic wave reflection member 13c. The photoacoustic wave reflection member 13c is transparent with respect to the excitation light L and is formed from a member with a different acoustic impedance than the right triangular prism 13b at the specimen S side, such as silicone oil or air. Since the difference between the acoustic impedance of the right triangular prism 13b and the acoustic impedance of the photoacoustic wave reflection member 13c satisfies a predetermined relationship, the photoacoustic wave U is reflected by the photoacoustic wave reflection member 13c.

The excitation light L passing through the objective lens 12 and the photoacoustic wave reflector 13 is focused on the focusing position of the objective lens 12. The specimen S is disposed so as to overlap with the focal spot of the excitation light L. The photoacoustic wave U generated at the focal spot position of the excitation light L in the specimen S is incident on the right triangular prism 13b. At the interface between the right triangular prism 13b and the photoacoustic wave reflection member 13c, the photoacoustic wave U is reflected in a different direction than the optical path of the excitation light L and exits from the right triangular prism 13b into the photoacoustic wave detection unit 152. The space between at least the objective lens 12 and the specimen S and between the right triangular prism 13b and the photoacoustic wave detection unit 152 is preferably filled with a photoacoustic wave transmission medium, such as water, through which the photoacoustic wave U easily propagates.

Figure 7:
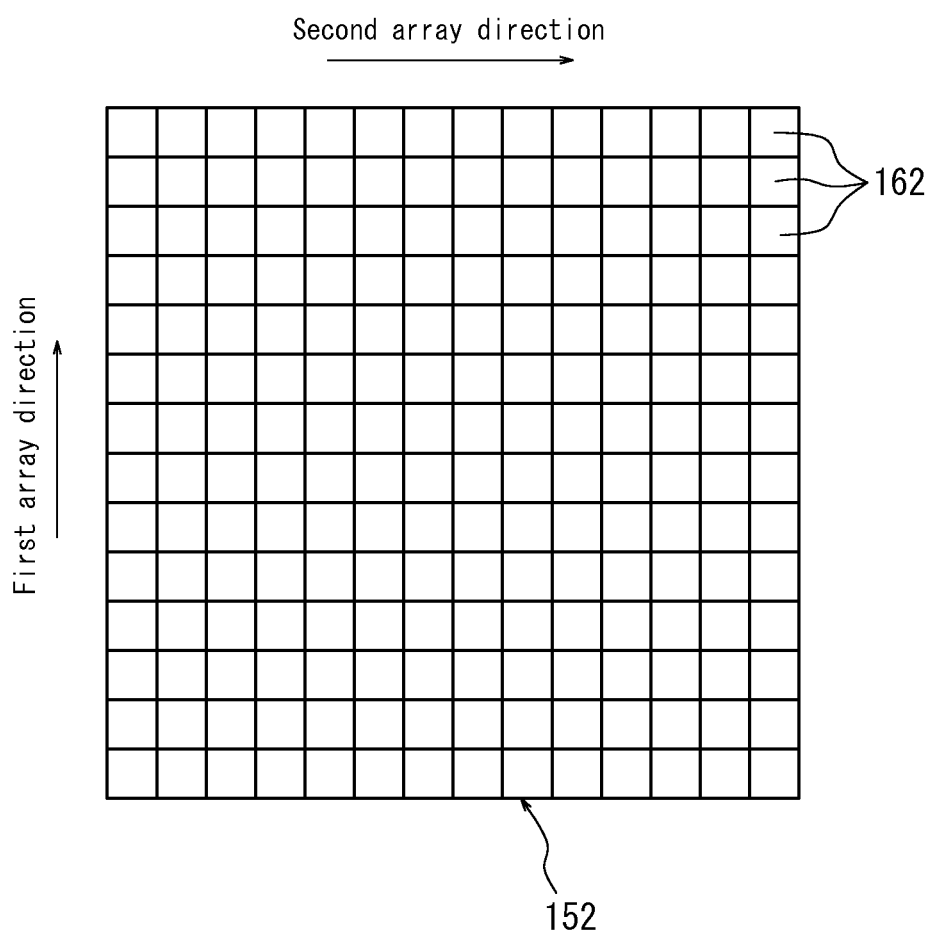
FIG. 7 is a layout drawing of detectors on the detection surface of the photoacoustic wave detection unit in FIG. 6.

The photoacoustic wave detection unit 152 includes a plurality of detectors 162 formed from, for example, an ultrasonic transducer. As illustrated in FIG. 7, the detectors 162 are arranged two-dimensionally along a first array direction corresponding to the first scanning direction and a second array direction corresponding to the second scanning direction. Each detector 162 detects the photoacoustic wave U exiting from the right triangular prism 13b.

Figure 8:
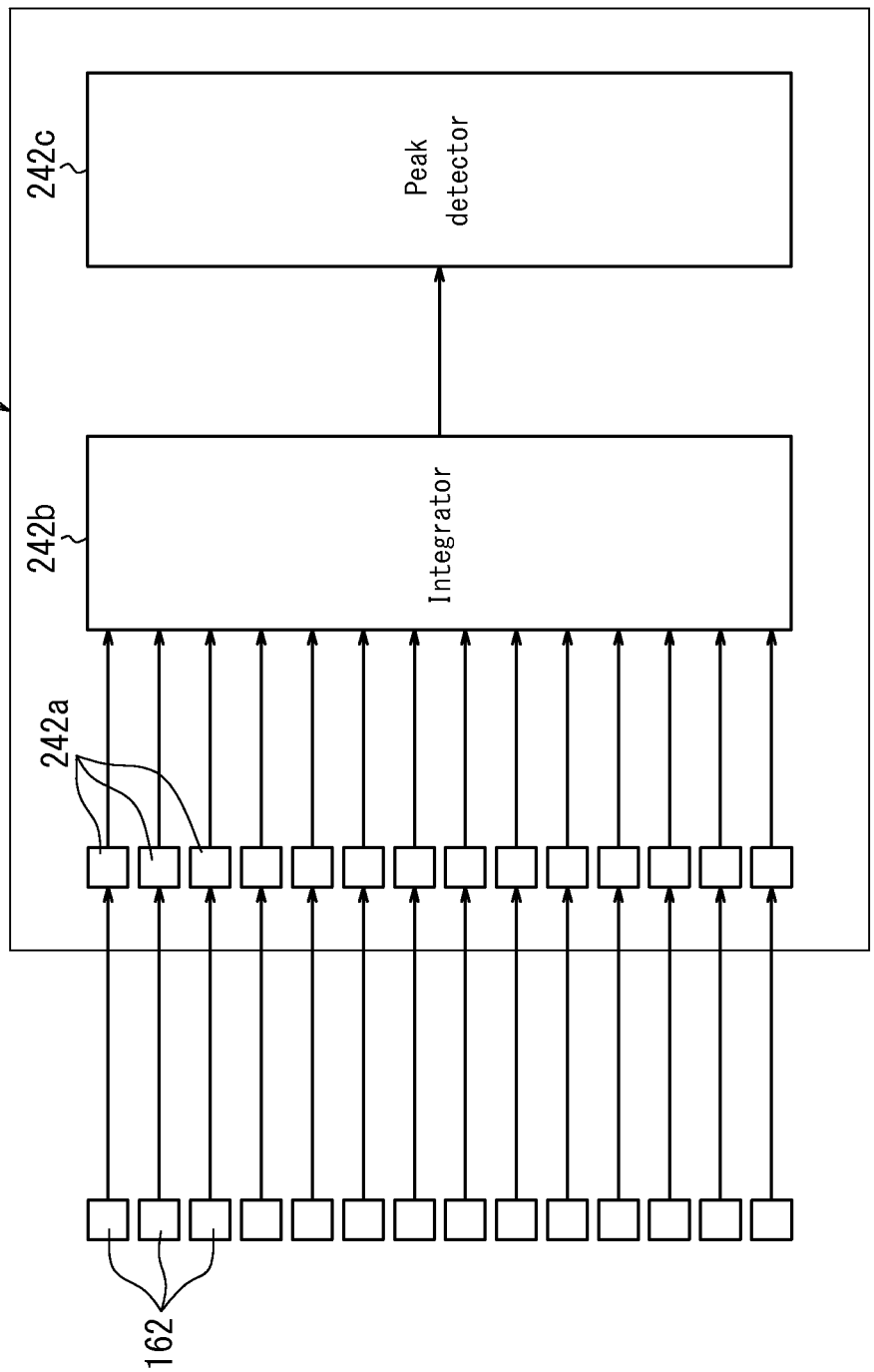
FIG. 8 is a functional block diagram schematically illustrating the internal structure of the combination unit in FIG. 6.

As illustrated in FIG. 8, a combination unit 242 includes delay devices 242a, an integrator 242b, and a peak detector 242c. So as to align the phases of the photoacoustic waves U detected by the detectors 162 arranged along the first array direction and the second array direction, the delay devices 242a delay the phases. Instead of a structure to delay the phases using delay devices 242a, phase adjustment of the photoacoustic waves U may be implemented with a structure to advance a relatively slow phase. The integrator 242b integrates, i.e. combines, the photoacoustic waves U detected by the delay devices 242a. The peak detector 242c detects, as a detection signal, the peak value of the photoacoustic wave U combined by the integrator 242b and outputs the detection signal.

The control processor 202 controls overall operations by the photoacoustic microscope 302. A memory 22 is connected to the control processor 202. The memory 22 stores a database compilation of the delay amount of each delay device 242a in association with the focal spot positions of the excitation light L so as to align the phases of the photoacoustic waves U detected by the detectors 162. The relationship between the delay amount and the associated focal spot position is calculated in advance and stored for the focal length of each objective lens that is mountable in the photoacoustic microscope. The control processor 202 reads the relationship, between the delay amount and the associated focal spot position, corresponding to the focal length of the mounted objective lens 13 from the memory 22 and controls the combination unit 242 in synchronization with scanning of the excitation light L by the light scanning unit 12.

A signal processor 23 is also connected to the control processor 202. In synchronization with the driving of the light scanning unit 12 by the control processor 202, i.e. in synchronization with the irradiation timing of the excitation light L when two-dimensionally scanning the specimen S in a plane orthogonal to the optical axis O of the objective lens 12, the signal processor 23 converts, based on a detection signal obtained from the combination unit 242, the correspondence relationship between the irradiation position of the excitation light L and the detection signal into data.

According to the photoacoustic microscope of Embodiment 4, the photoacoustic wave U from the specimen S is detected by each detector 162, the different phases in the detectors 162 are aligned, and the result is combined.

Figure 9:
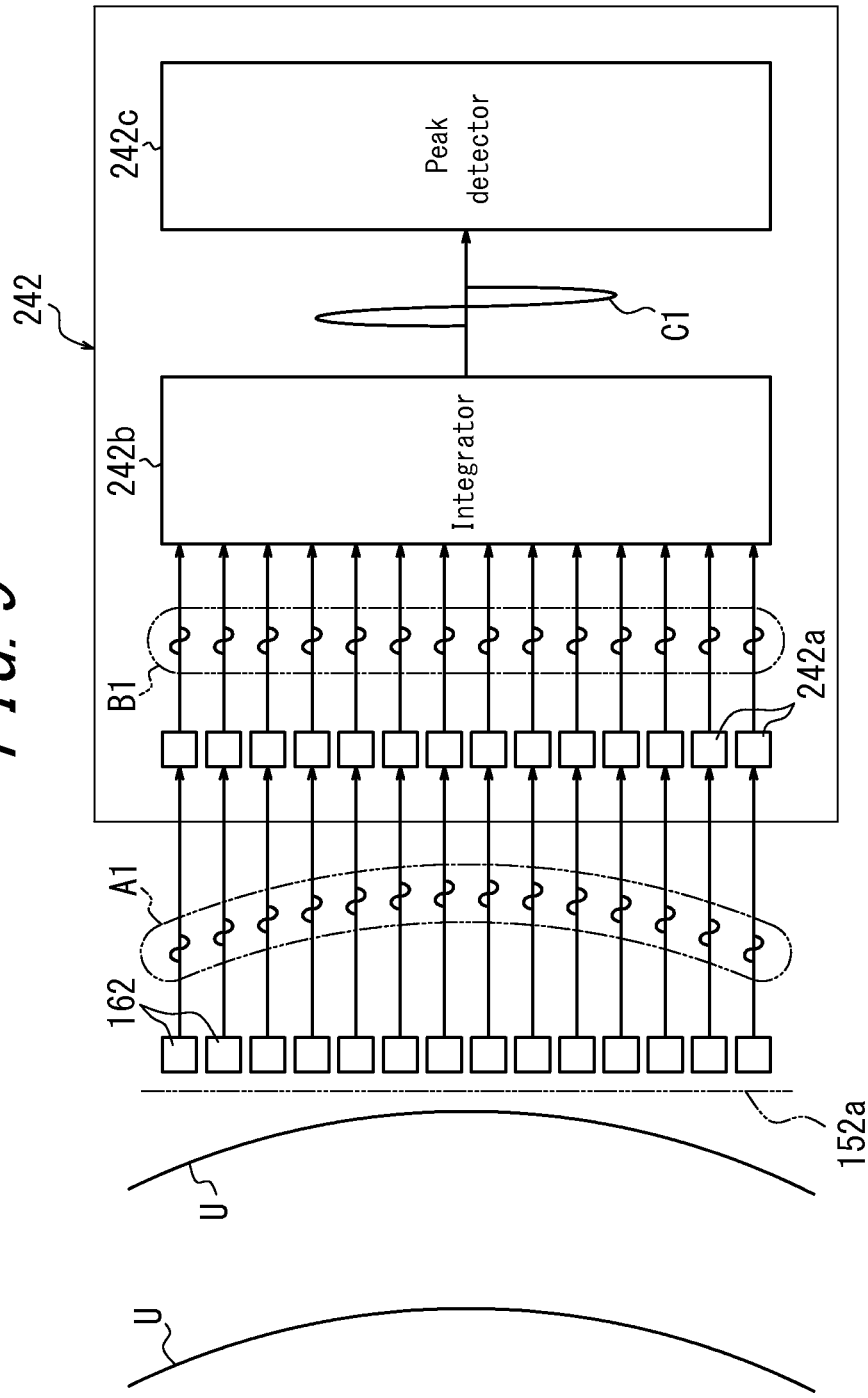
FIG. 9 is the first figure for illustrating phase adjustment in the combination unit.

For example, at a drive position of the light scanning unit 11 such that the focal spot of the excitation light L is formed along the optical axis O, a photoacoustic wave U that has a curved wavefront is incident on the detectors 162 from a direction perpendicular to the detection surface 152a, as illustrated in FIG. 9. In the case of a photoacoustic wave U with such a wavefront, the phase of the photoacoustic wave U detected by the detectors 162 has a peak near the center and is increasingly delayed towards the edges (see reference sign "A1"). Therefore, by delaying the phase with a delay amount that increases towards the center, the phases of the photoacoustic waves U output from the delay devices 242a are aligned (see reference sign "B1"). By integrating the photoacoustic waves U with aligned phases, a detection signal with a large peak is generated (see reference sign "C1").

Figure 10:
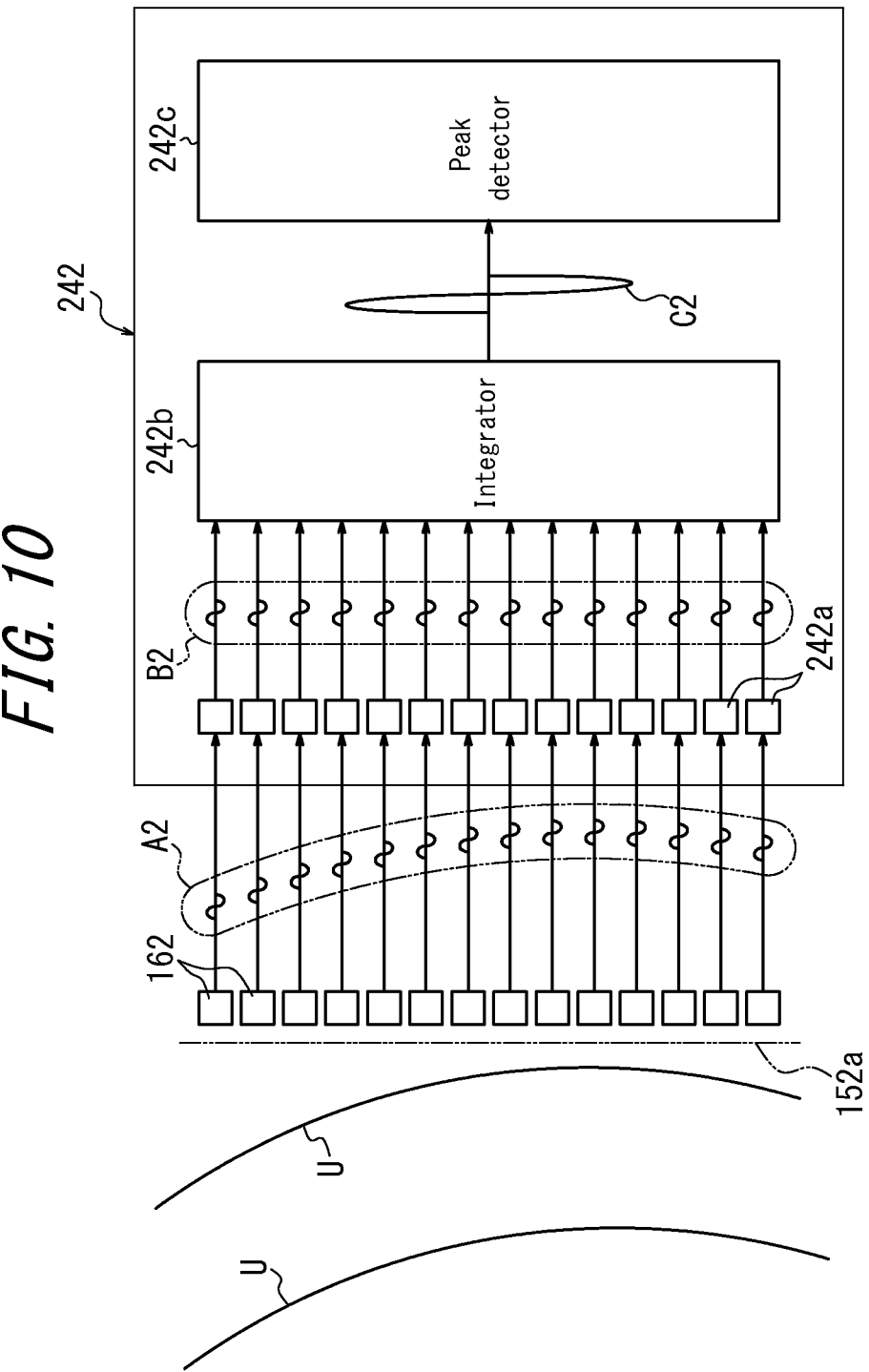
FIG. 10 is the second figure for illustrating phase adjustment in the combination unit.

At a drive position of the light scanning unit 11 such that the focal spot of the excitation light L is formed at a distance from the optical axis O of the objective lens 12, a photoacoustic wave U that has a curved wavefront is incident on the detectors 162 from a direction inclined with respect to a direction perpendicular to the detection surface 152a, as illustrated in FIG. 10. In the case of a photoacoustic wave U with such a wavefront, the phase of the photoacoustic wave U detected by the detectors 162 has a peak at a position shifted from the center towards one edge (downwards in FIG. 10) and is increasingly delayed towards the edges (see reference sign "A2"). Therefore, by delaying the phase with a delay amount that increases towards the peak position, the phases of the photoacoustic waves U output from the delay devices 242a are aligned (see reference sign "B2"). By integrating the photoacoustic waves U with aligned phases, a detection signal with a large peak is generated (see reference sign "C2").

Therefore, according to the photoacoustic microscope of Embodiment 4, the detection accuracy of the photoacoustic wave U from the specimen S can be improved across a wide scanning range of the specimen S. Scanning the specimen S by deflecting excitation light L with the light scanning unit 11 allows for high-speed scanning. Furthermore, since the relationship between the delay amount and the focal spot corresponding to the focal lengths of the mountable objective lenses is stored in the memory 22, the use of objective lenses with a variety of focal lengths can easily be accommodated. It is also possible to generate a detection signal with a large signal strength without using an acoustic lens.

Embodiment 5

Next, Embodiment 5 is described. Embodiment 5 differs from Embodiment 4 by including an acoustic lens and a drive unit. The structure and function of the photoacoustic wave detection unit and the function of the control processor also differ. The following description of Embodiment 5 focuses on the differences from Embodiment 4. Components that have the same structure as in Embodiment 4 are labeled with the same reference signs.

Figure 11:
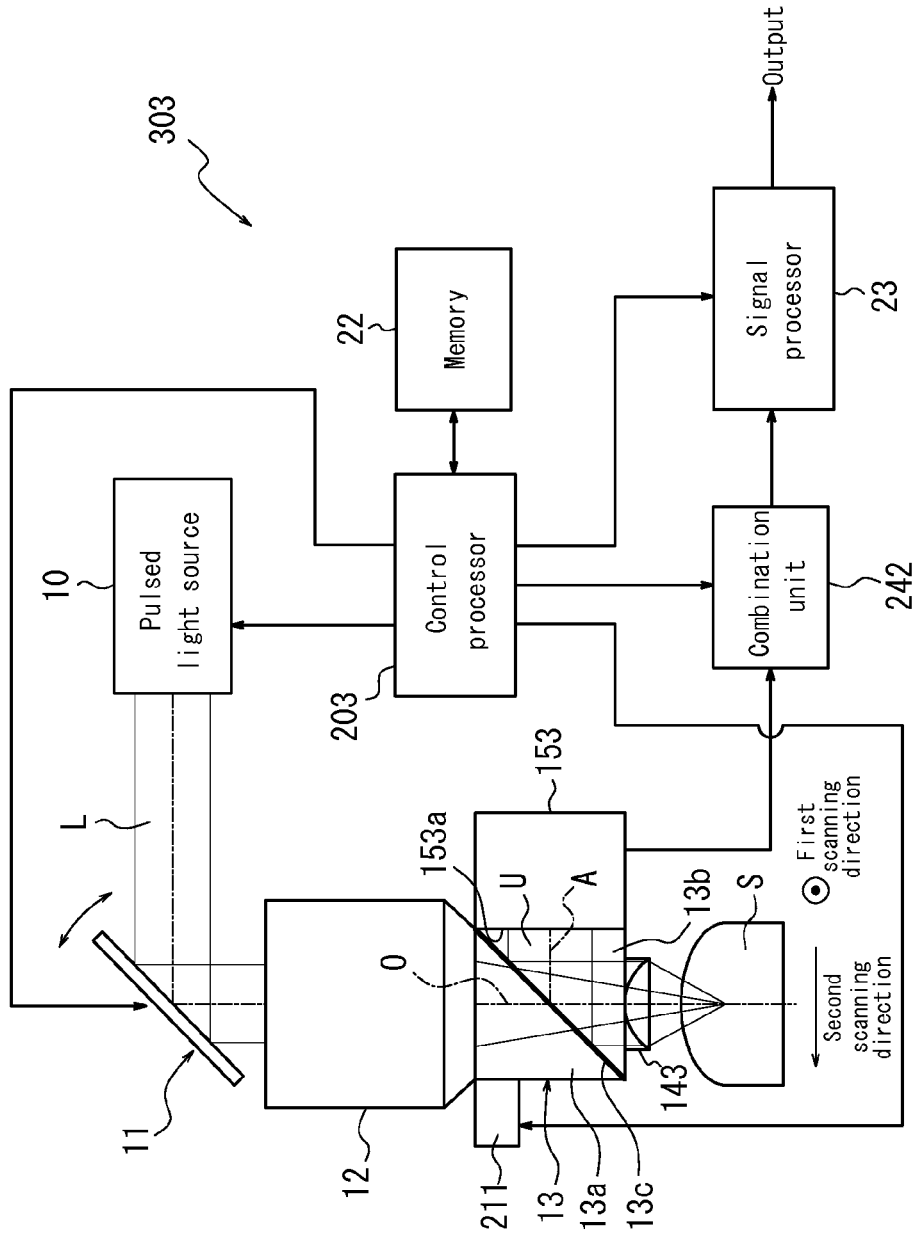
FIG. 11 schematically illustrates the structure of a section of a photoacoustic microscope according to Embodiment 5.

As illustrated in FIG. 11, a photoacoustic microscope 303 of this embodiment has a similar structure to the photoacoustic microscope 302 of Embodiment 4, with the addition of an acoustic lens 143 and a drive unit 211.

The acoustic lens 143 is joined to the exit face of the excitation light L in the right triangular prism 13b so that an acoustic axis A, which corresponds to the optical axis of an optical lens, is coaxial with an optical axis O of the objective lens 12. The acoustic wave focusing position of the acoustic lens 143 approximately matches the focusing position of the optical system constituted by the objective lens 12, photoacoustic wave reflector 13, and acoustic lens 143. In this way, the photoacoustic wave U generated at the focal spot position of the excitation light L in the specimen S is converted to a plane wave by the acoustic lens 143 and is incident on the right triangular prism 13b.

Figure 12:
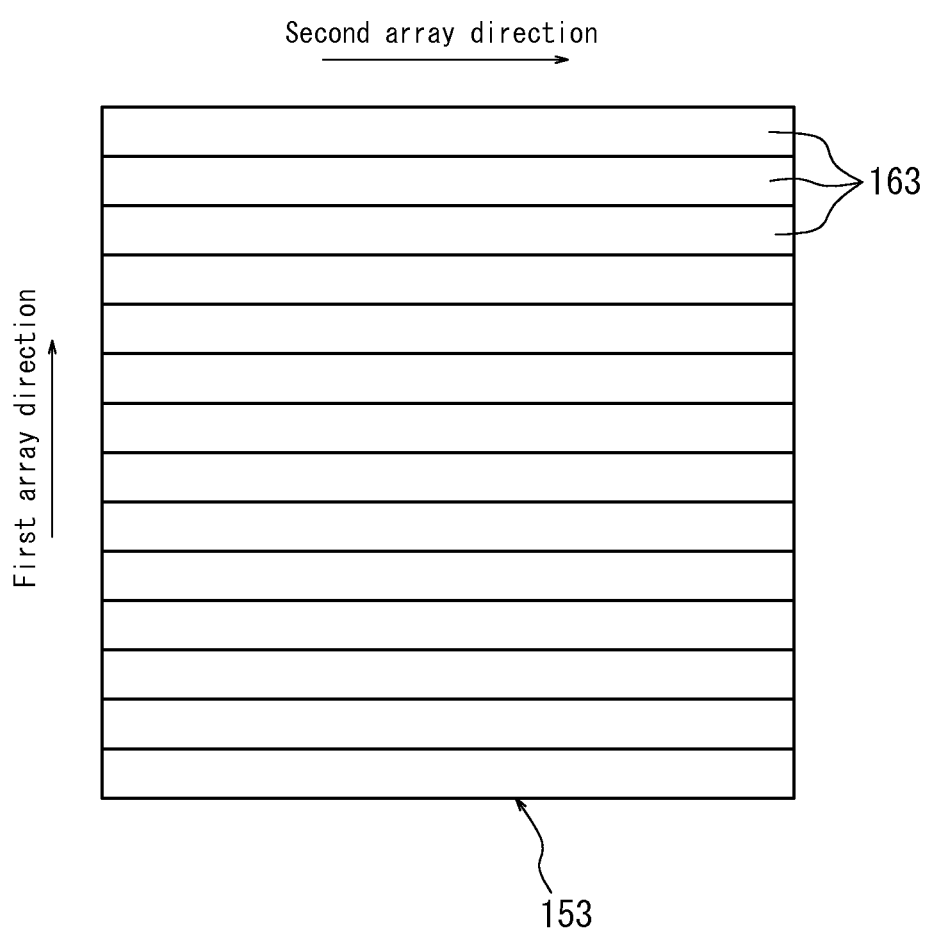
FIG. 12 is a layout drawing of detectors on the detection surface of the photoacoustic wave detection unit in FIG. 11.

The photoacoustic wave detection unit 153 is joined to the exit face of the photoacoustic wave U in the right triangular prism 13b, so that the acoustic axis A of the acoustic lens 143 and the detection surface 153a are orthogonal. In the photoacoustic wave detection unit 153, unlike Embodiment 4, detectors 163 are aligned only in the first array direction, as illustrated in FIG. 12. The first array direction is disposed so as to be parallel to the first scanning direction in FIG. 11.

As in Embodiment 3, the drive unit 211 for example includes a piezo actuator or stepping motor. Based on the control amount acquired from the control processor 203, the drive unit 211 displaces the photoacoustic wave reflector 13, photoacoustic wave detection unit 153, and acoustic lens 143 integrally along the second scanning direction.

The control processor 203 controls overall operations by the photoacoustic microscope 303. A memory 22 is connected to the control processor 203. The memory 22 stores a database compilation of the control amount of the drive unit 211 that is synchronized with scanning of the excitation light L by the light scanning unit 11 in association with the focal length of objective lenses that can be mounted in the photoacoustic microscope 303. The control amount represents the displacement amount of the photoacoustic wave reflector 13, photoacoustic wave detection unit 153, and acoustic lens 143. The control processor 203 reads the control amount (displacement amount) corresponding to the focal length of the mounted objective lens 12 from the memory 22 and controls the drive unit 211 in synchronization with scanning of the excitation light L by the light scanning unit 11.

According to the photoacoustic microscope of Embodiment 5, when moving the spot in the first scanning direction, the photoacoustic wave U from the specimen S is detected by each detector 163, the different phases in the detectors 163 are aligned in the first array direction, and the result is combined, as in Embodiment 4. In Embodiment 5, since the acoustic lens 143 is provided, the photoacoustic wave U is incident on the photoacoustic wave detection unit 153 as a plane wave, yet phase adjustment of the photoacoustic wave is performed on the plane wave as well, similar to Embodiment 4.

On the other hand, when driving the light scanning unit 11 in the second scanning direction, the photoacoustic wave reflector 13, photoacoustic wave detection unit 153, and acoustic lens 143 are integrally moved by the drive unit 211 along the second scanning direction in synchronization with scanning of the excitation light L by the light scanning unit 11, so that the plane wave, as seen from the first scanning direction, of the photoacoustic wave U from the specimen S is incident on the detection surface 153a of the photoacoustic wave detection unit 153 perpendicularly. In other words, at a drive position of the light scanning unit 11 such that the focal spot of the excitation light L is formed along the optical axis O of the objective lens 12, the focusing position of the acoustic lens 143 is controlled to match the focal spot position of the excitation light L, as illustrated in FIG. 13A. Therefore, with respect to the second scanning direction in Embodiment 5, in synchronization with scanning of the excitation light L by the light scanning unit 11, the acoustic lens 143 is moved by the drive unit 211 integrally with the photoacoustic wave reflector 13 and photoacoustic wave detection unit 153 in the second scanning direction, so that the focusing position of the acoustic lens 143 matches the focal spot position of the excitation light L.

Hence, the photoacoustic microscope according to this embodiment achieves effects similar to those of the photoacoustic microscope according to Embodiment 4.

It is to be noted that various changes and modifications will be apparent to those skilled in the art based on the drawings and embodiments described in this disclosure. Therefore, such changes and modifications are to be understood as included within the scope of the disclosure.

For example, in Embodiment 3, the photoacoustic wave detection unit 15 may be disposed at a distance from the photoacoustic wave reflector 13, as in Embodiment 2, and the photoacoustic wave reflector 13 and acoustic lens 14 may be moved integrally by the drive unit 211. In this embodiment, the control amount of the drive unit does not have to be stored in database form in the memory. The drive unit may instead be controlled based on output from a hardware or software-based function generation circuit or the like. Therefore, the memory is not an essential component in this disclosure. Furthermore, the light scanning unit may, for example, include one galvanometer mirror and perform main scanning of the focal spot with the galvanometer mirror, while secondary scanning may be performed by moving a specimen stage on which the specimen S is placed. In this case, the drive unit can omit displacement control corresponding to the secondary scanning direction.

In Embodiment 4, the acoustic lens 143 may be provided as in Embodiment 5. By providing the acoustic lens 143, the photoacoustic wave U with a curved front can be converted to a plane wave for detection by the detectors 162. By conversion to a plane wave, the delay amount is linearized and reduced, as illustrated in FIG. 14, thereby allowing for an increase in the detection accuracy of the photoacoustic wave detection unit 152.

In Embodiment 5, the structure such that the plane wave, as seen from the first scanning direction, of the photoacoustic wave U from the specimen S is incident on the detection surface 153a of the photoacoustic wave detection unit 153 perpendicularly is not limited to displacement, by the drive unit 211, of the photoacoustic wave reflector 13, photoacoustic wave detection unit 153, and acoustic lens 143.

Figure 15:
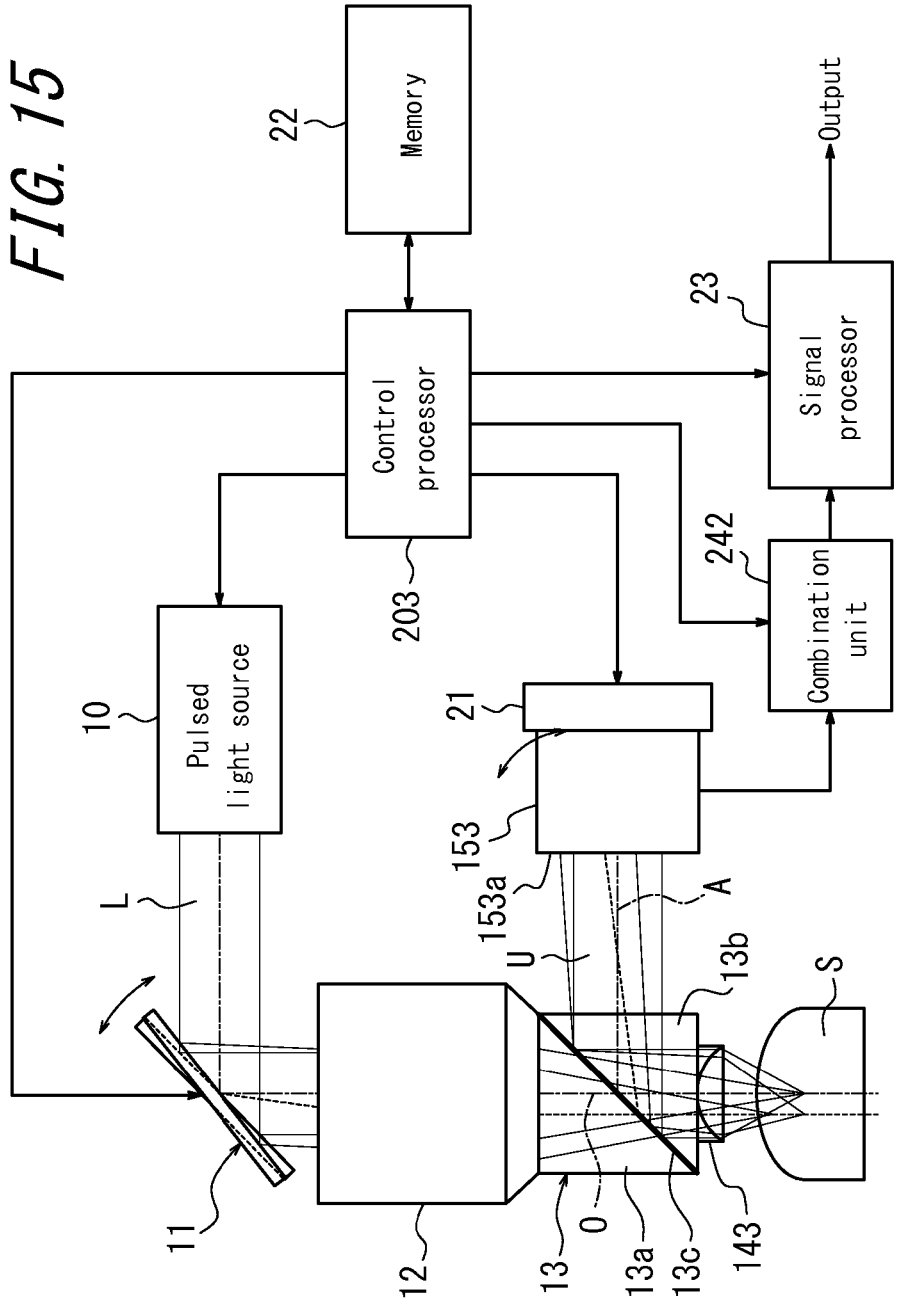
FIG. 15 schematically illustrates the structure of a section of the first modification to the photoacoustic microscope according to Embodiment 5.

For example, as illustrated in FIG. 15, the drive unit 21 may drive the photoacoustic wave detection unit 153, and in synchronization with scanning of excitation light L by the light scanning unit 11, control the inclination of the detection surface 153a of the photoacoustic wave detection unit 153 with respect to the acoustic axis A of the acoustic lens 143 based on a control amount from the control processor 203 so that the photoacoustic wave U is incident on the photoacoustic wave detection unit 153 perpendicularly.

Figure 16:
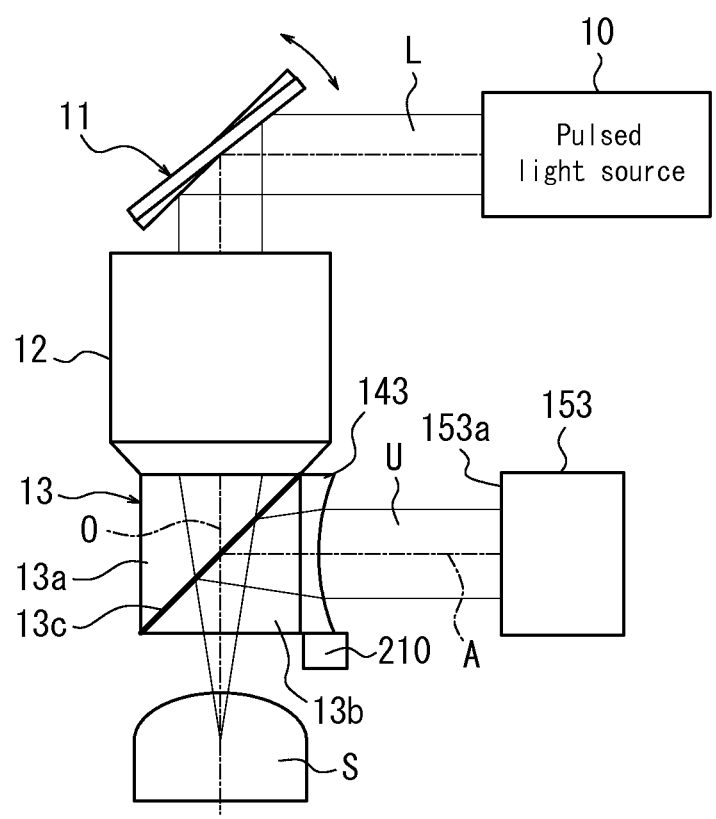
FIG. 16 schematically illustrates the structure of a section of the second modification to the photoacoustic microscope according to Embodiment 5.

As illustrated in FIG. 16, the acoustic lens 143 may also be displaceably joined to the exit face of the photoacoustic wave U in the right triangular prism 13b and may be moved along the exit face, i.e. in a plane orthogonal to the acoustic axis A, by the drive unit 210 based on the control amount from the control processor 203.

Figure 17:
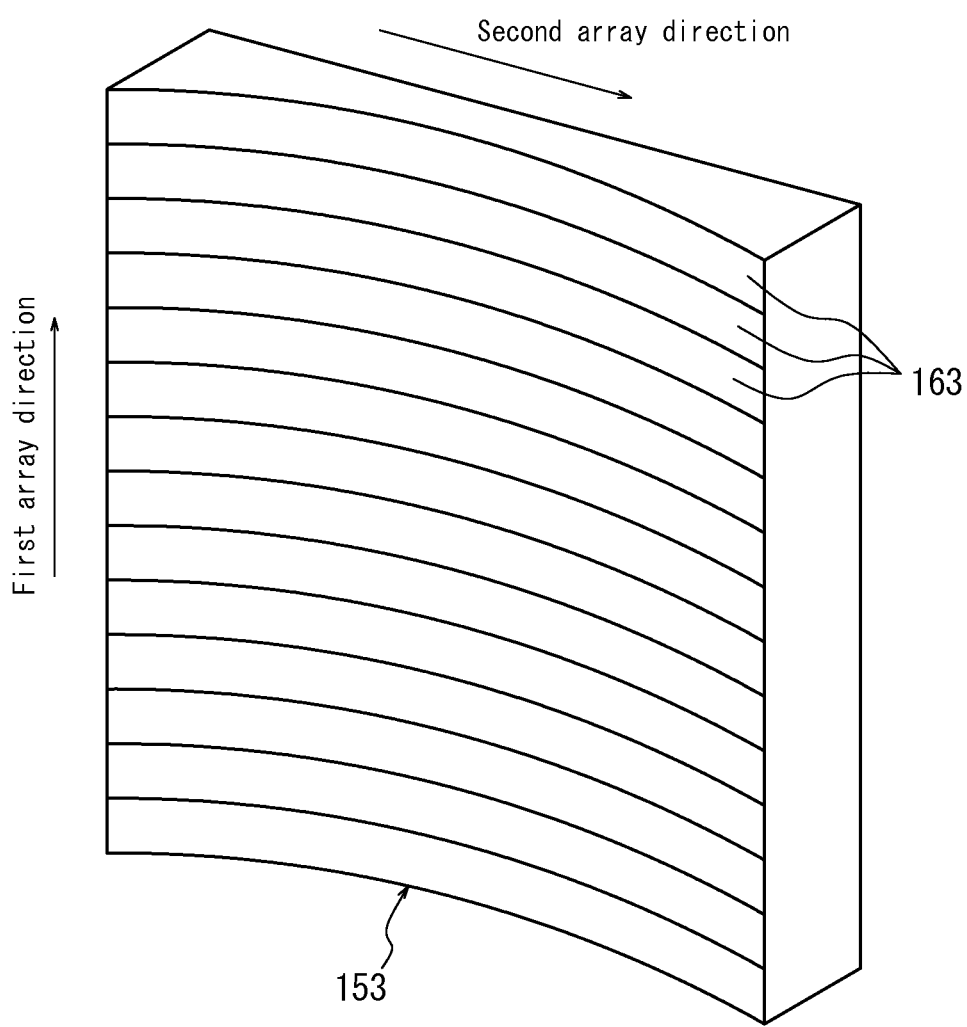
FIG. 17 is a perspective view illustrating the shape of the detection surface of the photoacoustic wave detection unit in the third modification to the photoacoustic microscope according to Embodiment 5.
Figure 18:
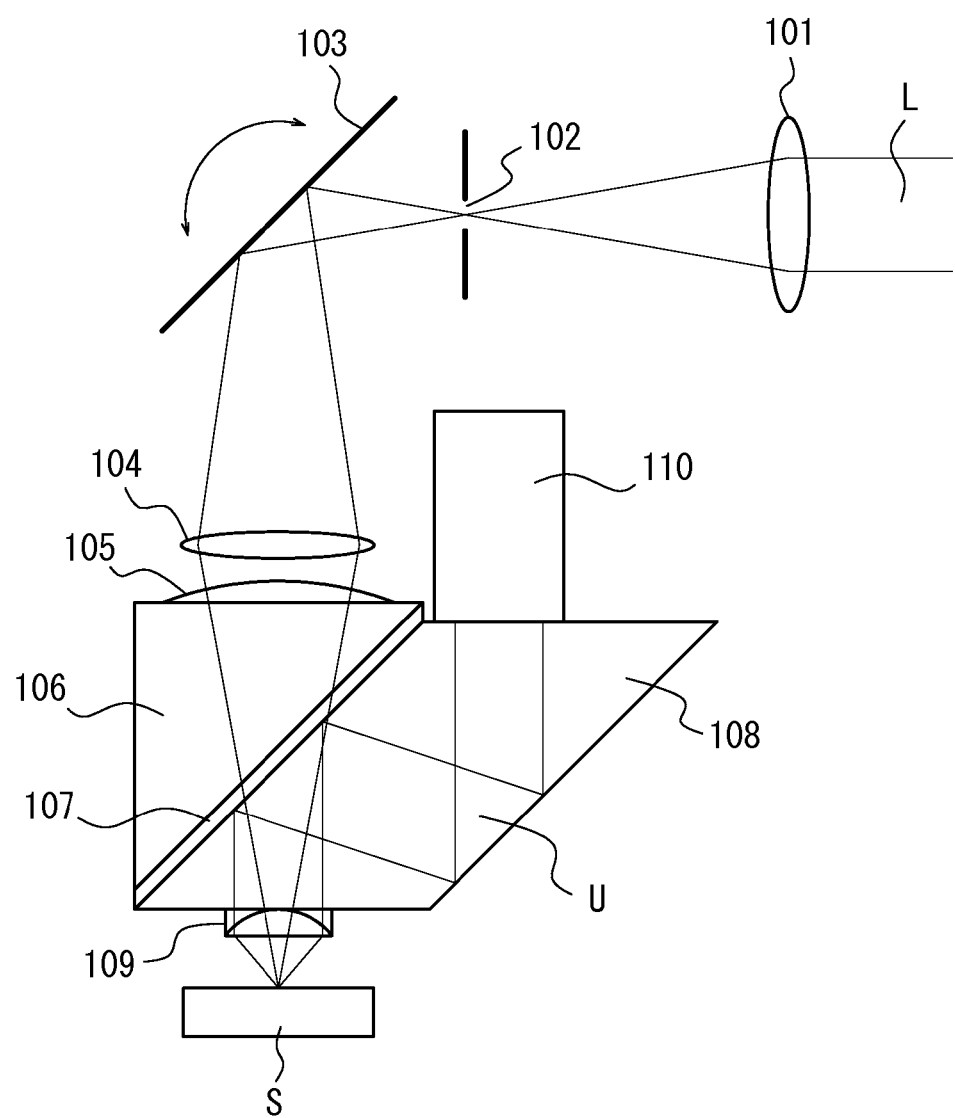
FIG. 18 schematically illustrates a conventional photoacoustic microscope.

In Embodiment 5, the light scanning unit may, for example, include one galvanometer mirror and perform main scanning of the focal spot along the first scanning direction with the galvanometer mirror, while secondary scanning may be performed by moving a specimen stage on which the specimen S is placed. In this case, the drive unit can omit displacement control corresponding to the secondary scanning direction. In this structure, the acoustic lens 143 may be omitted. When omitting the acoustic lens 143, however, in order to achieve highly-accurate detection of a photoacoustic wave U with a curved front in the second array direction, the detectors 163 are preferably arranged along a curve as viewed from the first array direction, and the surface on which the detectors 163 are arranged is preferably a curved surface (see FIG. 17).

In Embodiment 5, the photoacoustic wave detection unit 153 may similarly be disposed at a distance from the photoacoustic wave reflector 13, and the photoacoustic wave reflector 13 and acoustic lens 143 may be moved integrally by the drive unit 211.

In Embodiments 4 and 5, the control amount of the drive unit 211 and the relationship between the position of the focal spot and the delay amount do not have to be stored in database form in the memory 22. The drive unit 211 and combination unit 242 may instead be controlled based on output from a hardware or software-based function generation circuit or the like. Therefore, the memory is not an essential component in this disclosure.

REFERENCE SIGNS LIST

10 Pulsed light source
11 Light scanning unit
12 Objective lens
13 Photoacoustic wave reflector
13a, 13b Right triangular prism
13c Photoacoustic wave reflection member
14, 143 Acoustic lens
15, 152, 153 Photoacoustic wave detection unit
15a, 152a, 153a Detection surface
162, 163 Detector
20, 202, 203 Control processor
21, 210, 211 Drive unit
22 Memory
23 Signal processor
242 Combination unit
242a Delay device
242b Integrator
242c Peak detector
30, 300, 301, 302, 303 Photoacoustic microscope
L Excitation light
U Photoacoustic wave
S Specimen

The invention claimed is:

1. A photoacoustic microscope comprising:
an objective lens configured to irradiate a specimen with excitation light;
a light scanner configured to deflect the excitation light to scan the specimen;
an acoustic lens configured to convert a wavefront of a photoacoustic wave generated by the specimen due to irradiation with the excitation light;
a photoacoustic wave detector configured to detect the photoacoustic wave from the acoustic lens;
an actuator configured to physically move at least one of the acoustic lens and the photoacoustic wave detector; and
a controller configured to control the actuator, in synchronization with scanning of the excitation light by the light scanner, so that the photoacoustic wave is incident on the photoacoustic wave detector perpendicularly.

2. The photoacoustic microscope of claim 1, wherein the actuator moves a detection surface of the photoacoustic wave detector so as to incline with respect to an acoustic axis of the acoustic lens.

3. The photoacoustic microscope of claim 1, wherein the actuator moves at least the acoustic lens in a plane perpendicular to an acoustic axis of the acoustic lens.

4. The photoacoustic microscope of claim 1, further comprising a photoacoustic wave reflector between the objective lens and the specimen.

5. The photoacoustic microscope of claim 2, further comprising a photoacoustic wave reflector between the objective lens and the specimen.

6. The photoacoustic microscope of claim 3, further comprising a photoacoustic wave reflector between the objective lens and the specimen.

7. The photoacoustic microscope of claim 1, further comprising:
a memory configured to store a control amount of the actuator synchronized with scanning of the excitation light by the light scanner, wherein the controller controls the actuator drive unit based on the control amount stored in the memory.

8. The photoacoustic microscope of claim 2, further comprising:
a memory configured to store a control amount of the actuator synchronized with scanning of the excitation light by the light scanner, wherein the controller controls the actuator based on the control amount stored in the memory.

9. The photoacoustic microscope of claim 3, further comprising:
a memory configured to store a control amount of the actuator synchronized with scanning of the excitation light by the light scanner, wherein the controller controls the actuator drive unit based on the control amount stored in the memory.

10. The photoacoustic microscope of claim 4, further comprising:
a memory configured to store a control amount of the actuator synchronized with scanning of the excitation light by the light scanner, wherein the controller controls the actuator based on the control amount stored in the memory.

11. The photoacoustic microscope of claim 7,
wherein objective lenses each with a different focal length are mountable as the objective lens,
wherein the memory stores the control amount in association with the focal length of each objective lens that is mountable, and wherein the controller controls the actuator based on the control amount stored in the memory in association with the focal length of the objective lens that is mounted.

12. A photoacoustic microscope comprising:
an objective lens configured to irradiate a specimen with excitation light; a light scanner configured to deflect the excitation light to scan the specimen along at least a first scanning direction;
a photoacoustic wave detection unit comprising a plurality of detectors that detect a photoacoustic wave generated by the specimen due to irradiation with the excitation light, the detectors being arranged along a first array direction corresponding to the first scanning direction;

a combination unit configured to combine a phase of the photoacoustic wave detected by each detector;

an acoustic lens configured to convert a wavefront of the photoacoustic wave generated by the specimen due to irradiation with the excitation light;

an actuator configured to physically move at least one of the acoustic lens and the photoacoustic wave detection unit; and a controller configured to control the actuator, in synchronization with scanning of the excitation light along a second scanning direction by the light scanner, so that the photoacoustic wave is incident on the photoacoustic wave detection unit perpendicularly, wherein the light scanner also deflects the excitation light in the second scanning direction which differs from the first scanning direction, and wherein the plurality of detectors detect the photoacoustic wave that has the wavefront converted by the acoustic lens.

13. The photoacoustic microscope of claim 12, wherein the plurality of detectors are arranged on a surface of the photoacoustic wave detection unit, and the surface comprises a curved surface.

14. The photoacoustic microscope of claim 12, wherein objective lenses each with a different focal length are mountable as the objective lens; and wherein the combination unit combines the phase of the photoacoustic wave based on the focal length.

15. The photoacoustic microscope of claim 13, wherein objective lenses each with a different focal length are mountable as the objective lens; and wherein the combination unit combines the phase of the photoacoustic wave based on the focal length.

16. The photoacoustic microscope of claim 12, wherein the light scanner deflects the excitation light so as to scan also in a second scanning direction differing from the first scanning direction, and wherein in the photoacoustic wave detection unit, the plurality of detectors are arranged along a second array direction corresponding to the second scanning direction.

17. The photoacoustic microscope of claim 13, wherein the light scanner deflects the excitation light so as to scan also in a second scanning direction differing from the first scanning direction, and wherein in the photoacoustic wave detection unit, the plurality of detectors are arranged along a second array direction corresponding to the second scanning direction.

18. The photoacoustic microscope of claim 14, wherein the light scanner deflects the excitation light so as to scan also in a second scanning direction differing from the first scanning direction, and wherein in the photoacoustic wave detection unit, the plurality of detectors are arranged along a second array direction corresponding to the second scanning direction.

* * * * *